US008455186B2

(12) United States Patent
Smith et al.

(10) Patent No.: US 8,455,186 B2
(45) Date of Patent: Jun. 4, 2013

(54) METHOD OF DETECTION OF MICROORGANISMS WITH ENHANCED BACTERIOPHAGE AMPLIFICATION

(75) Inventors: Jonathan Drew Smith, Boulder, CO (US); Jon C. Rees, Snellville, GA (US); Duane Bush, Fort Collins, CO (US); Breanna Leigh Dreiling, Longmont, CO (US); Maria Izzo, Longmont, CO (US); Breanna Christine Smith, Lyons, CO (US); Bernard Sportmann, Longmont, CO (US); Tiffany Steinmark, Golden, CO (US); Richard Proctor, Madison, WI (US)

(73) Assignee: MicroPhage™ Incorporated, Longmont, CO (US)

(*) Notice: Subject to any disclaimer, the term of this patent is extended or adjusted under 35 U.S.C. 154(b) by 419 days.

(21) Appl. No.: 12/663,686

(22) PCT Filed: Jun. 13, 2008

(86) PCT No.: PCT/US2008/066962
§ 371 (c)(1),
(2), (4) Date: Apr. 6, 2010

(87) PCT Pub. No.: WO2008/157384
PCT Pub. Date: Dec. 24, 2008

(65) Prior Publication Data
US 2010/0196877 A1    Aug. 5, 2010

Related U.S. Application Data

(60) Provisional application No. 60/934,781, filed on Jun. 15, 2007.

(51) Int. Cl.
C12Q 1/70    (2006.01)
C12Q 1/02    (2006.01)

(52) U.S. Cl.
USPC .................................................. 435/5; 435/29

(58) Field of Classification Search
None
See application file for complete search history.

(56) References Cited

U.S. PATENT DOCUMENTS

| | | |
|---|---|---|
| 4,104,126 A | 8/1978 | Young |
| 4,797,363 A | 1/1989 | Teodorescu et al. |
| 4,861,709 A | 8/1989 | Ulitzur et al. |
| 5,085,982 A | 2/1992 | Keith |
| 5,168,037 A | 12/1992 | Entis et al. |
| 5,476,768 A | 12/1995 | Pearson et al. |
| 5,498,525 A | 3/1996 | Rees et al. |
| 5,620,845 A | 4/1997 | Gould et al. |
| 5,656,424 A | 8/1997 | Jurgensen et al. |
| 5,658,747 A | 8/1997 | Feldsine et al. |
| 5,679,510 A | 10/1997 | Ray et al. |
| 5,710,005 A | 1/1998 | Rittenburg |
| 5,723,330 A | 3/1998 | Rees et al. |
| 5,789,174 A | 8/1998 | Mouton et al. |
| 5,824,468 A | 10/1998 | Scherer et al. |
| 5,888,725 A | 3/1999 | Sanders et al. |
| 5,914,240 A | 6/1999 | Sanders et al. |
| 5,958,675 A | 9/1999 | Wicks et al. |
| 5,985,596 A | 11/1999 | Wilson et al. |
| 6,037,118 A | 3/2000 | Thomas et al. |
| 6,090,541 A | 7/2000 | Wicks et al. |
| 6,265,169 B1 | 7/2001 | Cortese et al. |
| 6,300,061 B1 | 10/2001 | Jacobs, Jr. et al. |
| 6,355,445 B2 | 3/2002 | Cherwonogrodzky et al. |
| 6,428,976 B1 | 8/2002 | Chang et al. |
| 6,436,652 B1 | 8/2002 | Cherwonogrodzky et al. |
| 6,436,661 B1 | 8/2002 | Adams et al. |
| 6,461,833 B1 | 10/2002 | Wilson et al. |
| 6,524,809 B1 | 2/2003 | Wilson et al. |
| 6,544,729 B2 | 4/2003 | Sayler et al. |
| 6,555,312 B1 | 4/2003 | Nakayama et al. |
| 6,660,437 B2 | 12/2003 | Friedrich et al. |
| 6,660,470 B1 | 12/2003 | Sanders et al. |
| 6,681,230 B1 | 1/2004 | Blott et al. |
| 6,861,230 B1 * | 3/2005 | Murphy et al. .............. 435/7.32 |
| 7,166,425 B2 | 1/2007 | Madonna et al. |
| 2002/0045195 A1 | 4/2002 | Hubscher et al. |
| 2002/0127547 A1 | 9/2002 | Miller |
| 2002/0192676 A1 | 12/2002 | Madonna et al. |
| 2003/0027241 A1 | 2/2003 | Sayler et al. |
| 2003/0032036 A1 | 2/2003 | Agrawal et al. |
| 2003/0152589 A1 | 8/2003 | Ramachandran et al. |
| 2004/0121403 A1 | 6/2004 | Miller |
| 2004/0137430 A1 | 7/2004 | Anderson et al. |
| 2004/0224359 A1 | 11/2004 | Madonna et al. |
| 2005/0003346 A1 | 1/2005 | Voorhees et al. |

FOREIGN PATENT DOCUMENTS

| | | |
|---|---|---|
| DE | 4314998 A1 | 11/1994 |
| EP | 0168933 A2 | 1/1986 |

(Continued)

OTHER PUBLICATIONS

Guttman et al., Bacteriophages:Biology and Applications, Edited by Elizabeth Kutter and Alexander Sulakvelidze, CRC Press, 2004.*

(Continued)

*Primary Examiner* — Zachariah Lucas
*Assistant Examiner* — Nicole Kinsey White
(74) *Attorney, Agent, or Firm* — Patton Boggs LLP

(57) ABSTRACT

A method of determining the presence or absence of a target microorganism in a sample to be tested, the method comprising: combining with the sample an amount of bacteriophage capable of attaching to the target microorganism to create a bacteriophage exposed sample, and a substance which enhances bacteriophage amplification or sensitivity; providing conditions to the bacteriophage-exposed sample sufficient to allow the bacteriophage to infect the microorganism; and assaying the bacteriophage-exposed sample to detect the presence or absence of a bacteriophage marker to determine the presence or absence of the target microorganism.

2 Claims, 4 Drawing Sheets

FOREIGN PATENT DOCUMENTS

| EP | 0228975 A1 | 7/1987 |
|---|---|---|
| EP | 0439354 | 7/1991 |
| EP | 1300082 | 4/2003 |
| WO | WO-8504189 | 9/1985 |
| WO | WO-8804326 | 6/1988 |
| WO | WO 92/02633 * | 2/1992 |
| WO | WO-9317129 | 9/1993 |
| WO | WO-9406931 | 3/1994 |
| WO | WO-9505483 A1 | 2/1995 |
| WO | WO-9818962 | 5/1998 |
| WO | WO-0010013 | 2/2000 |
| WO | WO-0125395 A1 | 4/2001 |
| WO | WO-02061117 A1 | 8/2002 |
| WO | WO-03087772 A2 | 10/2003 |
| WO | WO-2006012371 A1 | 2/2006 |
| WO | WO-2006083292 | 8/2006 |
| WO | WO-2006105504 A1 | 10/2006 |
| WO | WO-2008005268 A1 | 1/2008 |
| WO | WO-2008064241 A2 | 5/2008 |

OTHER PUBLICATIONS

Guttman et al., Bacteriophages:Biology and Applications, Edited by Elizabeth Kutter and Alexander Sulakvelidze, CRC Press 2004.*
Mills et al., Infect. Immun., 1986, 53(3):663.*
Taussig, Canadian Journal of Microbiology, 1960, 6(6):619-629.*
Taussig et al., Archives of Biochemistry and Biophysics, 1957, 69:524-534 (Abstract).*
In the US Patent and Trademark Office, U.S. Appl. No. 10/249,452, Non-Final Office Action dated Feb. 23, 2005, 12 pages; and corresponding response dated Aug. 26, 2005, 17 pages.
In the US Patent and Trademark Office, U.S. Appl. No. 10/249,452, Non-Final Office Action dated Feb. 7, 2006, 9 pages; and corresponding response dated Aug. 7, 2006, 7 pages, and supplemental response dated Aug. 30, 2006, 6 pages.
In the US Patent and Trademark Office, U.S. Appl. No. 10/823,294, Non-Final Office Action dated Jul. 23, 2007, 20 pages; and corresponding response dated Nov. 21, 2007, 24 pages, including Terminal Disclaimer.
In the US Patent and Trademark Office, U.S. Appl. No. 10/823,294, Final Office Action dated Dec. 3, 2007, 14 pages; and corresponding response dated Mar. 3, 2008, 14 pages, including Request for Continued Examination.
In the US Patent and Trademark Office, U.S. Appl. No. 10/823,294, Non-Final Office Action dated Apr. 25, 2008, 11 pages; and corresponding response dated Aug. 25, 2008, 5 pages.
In the US Patent and Trademark Office, U.S. Appl. No. 10/823,294, Non-Final Office Action dated Sep. 30, 2008, 8 pages.
In the US Patent and Trademark Office, U.S. Appl. No. 12/346,656, Non-Final Office Action dated Oct. 20, 2009, 17 pages.
Lindsay et al.; "The gene for toxic shock toxin is carried by a family of mobile pathogenicity islands in Staphylococcus aureus"; Molecular Microbiology; 1998; vol. 29, No. 2; pp. 527-543.
Madonna et al.; "Detection of Esherichia coli Using Immunomagnetic Separation and Bacteriophage Amplification Coupled With Matrix-Assisted Laser Desorption/Ionization Time-of-Flight Mass Spectrometry"; Rapid Communications in Mass Spectrometry; vol. 17; published online Dec. 24, 2002; pp. 257-263.
Bordner et al.; "Microbiological Methods for Monitoring the Environment"; EPA Report No. EPA-600/8-78-017; US Environmental Protection Agency, Cincinnati, Ohio 45268; Dec. 1978.
Cudjoe et al.; "Immunomagnetic Separation of Salmonella From Foods and Their Detection Using Immunomagnetic Particle"; International Journal of Food Microbiology; 27 (1995); pp. 11-25.
Dickinson et al.; "New and Improved Strategies for the Rapid Detection and Differential Identification of Microbial Spores Using MALDI-TOFMS"; Proceedings of the 50th ASMS Conference on Mass Spectrometry and Allied Topics; Orlando, Florida; Jun. 2-6, 2002.
Dubow, Michael S.; "Bacterial Identification—Use of Phages"; Academic Press Encyclopedia of Virology; May 18, 2003.

Dziadkowiec et al.; "The detection of Salmonella in skimmed milk powder enrichments using conventional methods and immunomagnetic separation"; Letters in Applied Microbiology; 1995; pp. 361-364; vol. 20.
Favrin et al.; "Development and Optimization of a Novel Immunomagnetic Separation-Bacteriophage Assay for Detection of Salmonella enterica Serovar Enteritidis in Broth"; Applied and Environmental Microbiology; Jan. 2001; pp. 217-224; vol. 67, No. 1.
Gantt et al.; "Use of an Internal Control for Matrix-Assisted Laser Desorption/Ionization Time-of-Flight Mass Spectrometry Analysis of Bacteria"; J Am Soc Mass Spectrom; 1999; pp. 1131-1137; vol. 10.
Grant et al.; "Isolation of Mycobacterium paratuberculosis from Milk by Immunomagnetic Separation"; Applied and Environmental Microbiology; Sep. 1998; pp. 3153-3158; vol. 64, No. 9.
Hirsh et al.; "Rapid Detection of Salmonella spp. by Using Felix-O1 Bacteriophage and High-Performance Liquid Chromatography"; Applied and Environmental Microbiology, 1983; 45(1):260-264.
In the US Patent and Trademark Office U.S. Appl. No. 11/933,083, Non-Final Office Action dated Jun. 18, 2010, 11 pages.
Jenison et al.; "Silicon-based biosensors for rapid detection of protein or nucleic acid targets"; Clin. Chem; 2001; pp. 1894-1900; vol. 47, No. 10.
Jenison et al.; "Thin film biosensor for rapid detection of mecA from Methicillin-resistant Staphylococcus aureus"; Clin. Chem.; 2000; pp. 1501-1504; vol. 46, No. 9.
Kingsbury et al.; "Rapid Detection and Identification of Infectious Agents"; Academic Press, Inc.; New York; 1985.
Kodikara et al.; "Near on-line detection of enteric bacteria using lux recombinant bacteriophage"; FEMS Microbiology Letters; 1991; pp. 261-266; vol. 83.
Lynn et al.; "Identification of Enterobacteriaceae Bacteria by Direct Matrix-assisted Laser Desorption/Ionization Mass Spectrometric Analysis of Whole Cells"; Rapid Communication in Mass Spectrometry; Rapid Commun. Mass Spectrom.; 1999; pp. 2022-2027; vol. 13.
Madonna et al.; "Detection of bacteria from biological mixtures using immunomagnetic separation combined with matrix-assisted laser desorption/ionization time-of-flight mass spectrometry"; Raid Communication in Mass Spectrometry; 2001; pp. 1068-1074; vol. 15.
Madonna et al.; "Detection of Escherichia coli using immunomagnetic separation and bacteriophage amplification coupled with matrix-assisted laser desorption/ionization time-of-flight mass spectrometry"; Rapid Communications in Mass Spectrometry, 2003, vol. 17, pp. 257-263.
Mandeville et al., "Diagnostic and Therapeutic Applications of Lytic Phages", 2003 Anal. Lett., 36, 15, 3241-3259.
Marei et al.; "Evaluation of a rapid bacteriophage-based method for the detection of Mycobacterium tuberculosis in clinical samples"; Journal of Medical Microbiology; 2003; vol. 52; pp. 331-335.
Olsvik et al.; "Magnetic separation techniques in diagnostic microbiology"; Clinical Microbiology Reviews; vol. 7, No. 1; pp. 43-54 (Jan. 1994).
Pyle et al.; "Sensitive Detection of Escherichia coli 0157:H7 in Food and Water by Immunomagnetic Separation and Solid-Phase Laser Cytometery"; Applied and Environmental Microbiology; May 1999; pp. 1966-1972.
Ryzhov et al.; "Characterization of the Protein Subset Desorbed by MALDI from Whole Bacterial Cells"; Analytical Chemistry; Feb. 15, 2001; pp. 746-750; vol. 73, No. 4.
Saiyed et al.; "Application of magnetic techniques in the field of drug discovery and biomedicine"; BioMagnetic Research and Technology; Sep. 18, 2003; vol. 1, No. 2; pp. 1-8.
Siuzdak; "Probing Viruses With Mass Spectrometry"; Journal of Mass Spectrometry; vol. 33; 1998; pp. 203-211.
Skjerve et al.; "Detection of Listeria monocytogenes in Foods by Immunomagnetic Separation"; Applied and Environmental Microbiology; Nov. 1990; pp. 3478-3481.
Stewart, G.S.A.B.; "In vivo bioluminescence: new potentials for microbiology"; Letters in Applied Microbiology; 1990; pp. 1-8; vol. 10.
Strauss et al.; "Purification and Properties of Bacteriophage MS2 and of its Ribonucleic Acid"; J. Mol. Biol.; 1963; pp. 43-54; vol. 7.

Van Der Wolf et al.; "Immunomagnetic separation of *Erwinia carotovora* subsp. atroseptica from potato peel extracts to improve detection sensitivity on a crystal violet pectate medium or by PCR"; Journal of Applied Bacteriology; 1996; pp. 487-495; vol. 80.

Wang et al.; "Investigation of Spectral Reproducibility in Direct Analysis of Bacteria Proteins by Matrix-assisted Laser Desorption/Ionization Time-of-flight Mass Spectrometry"; Rapid Communications in Mass Spectrometry; Rapid Commun. Mass Spectrom.; 1998; pp. 456-464; vol. 12.

Wyatt et al.; :Immunoassays for Food-poisoning Bacteria and Bacterial Toxins; James & James (Science Publishers) Ltd. and Chapman & Hall; London, Great Britain; 1992.

Yu et al.; "Immunomagnetic-Electrochemiluminescent Detection of *Escherichia coli* 0157 and *Salmonella typhimurium* in Foods and Environmental Water Samples"; Applied and Environmental Microbiology; Feb. 1996; pp. 587-592.

\* cited by examiner

METHOD OF DETECTION OF MICROORGANISMS WITH ENHANCED BACTERIOPHAGE AMPLIFICATION

CROSS-REFERENCE TO RELATED APPLICATIONS

This application is a national stage of PCT Patent Application No. PCT/US09/066962 filed Jun. 13, 2008, which claims the benefit of U.S. Provisional Patent Application No. 60/934,781 filed Jun. 15, 2007, The foregoing PCT and provisional applications are hereby incorporated by reference to the same extent as though fully disclosed herein.

FIELD OF THE INVENTION

The invention relates generally to the field of identification of microscopic living organisms, and more particularly to the identification of microorganisms using bacteriophage.

BACKGROUND OF THE INVENTION

Bacteriophage amplification has been suggested as a method to accelerate microorganism identification. See, for example, U.S. Pat. No. 5,985,596 issued Nov. 16, 1999 and U.S. Pat. No. 6,461,833 B1 issued October 8, both to Stuart Mark Wilson; U.S. Pat. No. 4,861,709 issued Aug. 29, 1989 to Ulitzur et al.; U.S. Pat. No. 5,824,468 issued Oct. 20, 1998 to Scherer et al.; U.S. Pat. No. 5,656,424 issued Aug. 12, 1997 to Jurgensen et al.; U.S. Pat. No. 6,300,061 B1 issued Oct. 9, 2001 to Jacobs, Jr. et al.; U.S. Pat. No. 6,555,312 B1 issued Apr. 29, 2003 to Hiroshi Nakayama; U.S. Pat. No. 6,544,729 B2 issued Apr. 8, 2003 to Sayler et al.; U.S. Pat. No. 5,888,725 issued Mar. 30, 1999 to Michael F. Sanders; U.S. Pat. No. 6,436,661 B1 issued Aug. 20, 2002 to Adams et al.; U.S. Pat. No. 5,498,525 issued Mar. 12, 1996 to Rees et al.; Angelo J. Madonna, Sheila VanCuyk and Kent J. Voorhees, "Detection Of *Escherichia Coli* Using Immunomagnetic Separation And Bacteriophage Amplification Coupled With Matrix-Assisted Laser Desorption/Ionization Time-Of-Flight Mass Spectrometry", Wiley InterScience, DOI:10.1002/rem.900, 24 Dec. 2002; and U. S. Patent Application Publication No. 2004/0224359 published Nov. 11, 2004, Bacteriophage are viruses that have evolved in nature to use bacteria as a means of replicating themselves. A bacteriophage (or phage) does this by attaching itself to a bacterium and injecting its genetic material into that bacterium, inducing it to replicate the phage from tens to thousands of times. Some bacteriophage, called lytic bacteriophage, rupture the host bacterium releasing the progeny phage into the environment to seek out other bacteria. The total incubation time for infection of a bacterium by parent phage, phage multiplication (amplification) in the bacterium to produce progeny phage, and release of the progeny phage after lysis can take as little as an hour depending on the phage, the bacterium, and the environmental conditions. Thus, it has been proposed that the use of bacteriophage amplification in combination with a test for bacteriophage or a bacteriophage marker may be able to significantly shorten the assay time as compared to a traditional substrate-based identification. A single infected bacterium may produce $10^1$-$10^4$ progeny bacteriophage, and each bacteriophage particle may contain $10^1$-$10^3$ copies of capsid or other structural proteins. Signal amplifications of $10^2$-$10^7$ from each infected bacterium, therefore, are possible, given an appropriate method of detecting progeny bacteriophage, bacteriophage nucleic acids, or bacteriophage proteins. Many methods known to the art are suitable for detection, including but not limited to, PCR, mass spectrometry, antibody or aptamer-based binding assays, and plaque assays.

In each of the bacteriophage amplification methods mentioned above, samples potentially containing target bacteria are incubated with bacteriophage specific for those bacteria. In the presence of the bacteria, the bacteriophage infect and replicate in the bacteria resulting in the production of a measurable signal indicating the presence of the target bacteria. Some methods utilize the detection of progeny phage released from infected target bacteria as a means of detection and identification. In this case, progeny phage are not produced if the parent phage do not successfully infect the target bacteria. Still other methods rely on the detection of phage replication products rather than whole progeny phage. For example, luciferase reporter bacteriophage produce luciferase when they successfully infect target bacteria. The luciferase then produces light that, if detected, indicates the presence of target bacteria in the sample. Other methods rely on the detection of bacterial debris that is released following a successful lytic infection of target bacteria by a specific bacteriophage. Still other methods rely only on the ability of bacteriophage to attach to the bacteria and do not employ amplification. To accurately identify the target bacteria, each of these phage-based diagnostic methods demands that the bacteriophage have both high sensitivity for the target bacteria and high specificity to avoid replication in non-target strains or species of bacteria. Finding or developing bacteriophage with those characteristics is very challenging. Thus, while bacteriophage amplification is considered as a promising process for detecting microorganisms, a commercially useful diagnostic process using bacteriophage that is competitive with conventional commercial microorganism detection processes has not yet been developed. Bacteriophage with acceptable sensitivity often lack sufficient specificity, i.e., they cross react with too many non-target bacteria. This lack of acceptable sensitivity in combination with sufficient specificity is a critical problem in commercializing bacteriophage diagnostic processes.

It is well known that, within a given bacterial species, individual strains vary in their susceptibility to bacteriophage strains; in fact, this differential susceptibility forms the basis of phage-typing schemes for the identification of bacterial strains. The biochemical basis of this differential susceptibility is not well understood, but some factors have been identified. These include virulence factors, often found on mobile genetic elements within bacterial chromosomes. A well-known example is the *Staphylococcus aureus* (*S. aureus*) factor for Toxic Shock Syndrome, encoded by the pathogenicity island SaPI1, found in approximately 20% of clinical isolates of *S. aureus*. These pathogenicity islands are mobilized by infection of the host bacterium by bacteriophages and are encapsidated into infectious particles. This mobilization and encapsidation takes place at the expense of the infecting bacteriophage, whose replication can be reduced by a factor of 100 fold (Lindsay et al., *Molecular Microbiology*, 1998, 29:2527). This reduction is problematic for any assay or process dependent upon bacteriophage amplification, as it renders a substantial fraction of bacterial hosts incapable of producing high bacteriophage yields.

Thus, there remains a need for a faster and more effective method of detecting microorganisms that achieves both specificity and sensitivity and, at the same time, the amplification remains high.

BRIEF SUMMARY OF THE INVENTION

The invention provides an advancement of the art and overcomes the above problems by the adding one or more substances to the bacteriophage-exposed sample, which substances enhance bacteriophage amplification without reducing specificity or sensitivity. It has been found, for example, that the expression of toxic shock proteins, as well as a variety of other *S. aureus* exoproteins, is suppressed by the presence of sub-lethal concentration of fatty acids and related compounds in the growth medium. We find that addition of fatty acids, conjugated fatty acids, fatty acid esters, or fatty acid amides to growth media significantly enhances the performance and utility of bacteriophage-based tests in detecting, identifying, and characterizing bacterial hosts for diagnostic and research purposes. As an example, we have shown that the addition of such fatty acids and related compounds substantially improves bacteriophage amplification on strains of *S. aureus* that are poor bacterial hosts, on strains of *S. aureus* that are good bacterial hosts, and that bacteriophage amplification by methicillin-resistant *S. aureus* (MRSA) strains grown in the presence of β-lactam antibiotics, such as cefoxitin, is also substantially improved.

Another substance that has been found to enhance bacteriophage amplification without reducing specificity or sensitivity is pyruvate in any of its various forms, such as pyruvic acid and sodium pyruvate. For example, the addition of 10 mmol/L (millimoles per liter) to 50 mmol/L of sodium pyruvate to a wide variety of *S. aureus* strains was found to significantly increase phage sensitivity. The addition of from 12 mmol/L to 37 mmol/L of sodium pyruvate was found to increase phage sensitivity in these strains from about 78% to between 87% and 92%. In the range of concentrations of from 15 mmol/L to 31 mmol/L, the sensitivity increased to above 90%. The most preferred concentration was 27 mmol/L, at which concentration the sensitivity was increased about 15% over sensitivities without sodium pyruvate. Similarly, the mean amplification of the bacteriophage was increased significantly in a range from about 10 mmol/L to 60 mmol/L sodium pyruvate. For example, the mean amplification increased from about 92 without sodium pyruvate to 150 at about 30 mmol/L of sodium pyruvate.

The invention provides a method of determining the presence or absence of a target microorganism in a sample to be tested, the method comprising: combining with the sample an amount of bacteriophage capable of attaching to the target microorganism to create a bacteriophage-exposed sample; providing conditions to the bacteriophage-exposed sample sufficient to allow the bacteriophage to infect the microorganism; and assaying the bacteriophage-exposed sample to detect the presence or absence of a bacteriophage marker to determine the presence or absence of the target microorganism; the method characterized by the combining, including combining with the bacteriophage and the target microorganism a substance which enhances bacteriophage amplification in the target organism or bacteriophage sensitivity to the target microorganism.

The invention also provides a medium for determining the presence or absence of a target microorganism in a sample to be tested, the medium comprising bacteriophage and characterized in that the medium includes a substance that enhances the replication of the bacteriophage in the target microorganism or enhances bacteriophage sensitivity to the target organism.

Preferably, the microorganism is a bacterium and the assaying comprises detecting the bacteriophage marker as an indication of the presence of the target bacterium in the sample. Preferably, the substance suppresses a bacterial virulence factor. Preferably, the virulence factor is a toxic shock protein. Preferably, the substance is a fatty acid compound. Preferably, the fatty acid compound is lauric acid. Preferably, the substance is selected from the group consisting of a fatty acid, a conjugated fatty acid, a fatty acid ester, and a fatty acid amide. Preferably, the substance comprises pyruvate. Preferably, the substance comprises sodium pyruvate. Preferably, the method further comprises inhibiting phage replication in a potentially cross-reactive, non-target microorganism. Preferably, the inhibiting comprises selectively removing potential cross-reactive bacteria from the sample using selective binding agents attached to a support, or selectively destroying potentially cross-reactive bacteria.

The invention solves the problem of enhancing the sensitivity of the bacteriophage amplification process while at the same time maintaining or enhancing the selectivity of a bacteriophage. Numerous other features, objects, and advantages of the invention will become apparent from the following description when read in conjunction with the accompanying drawings.

DETAILED DESCRIPTION OF THE INVENTION

Figure 1:
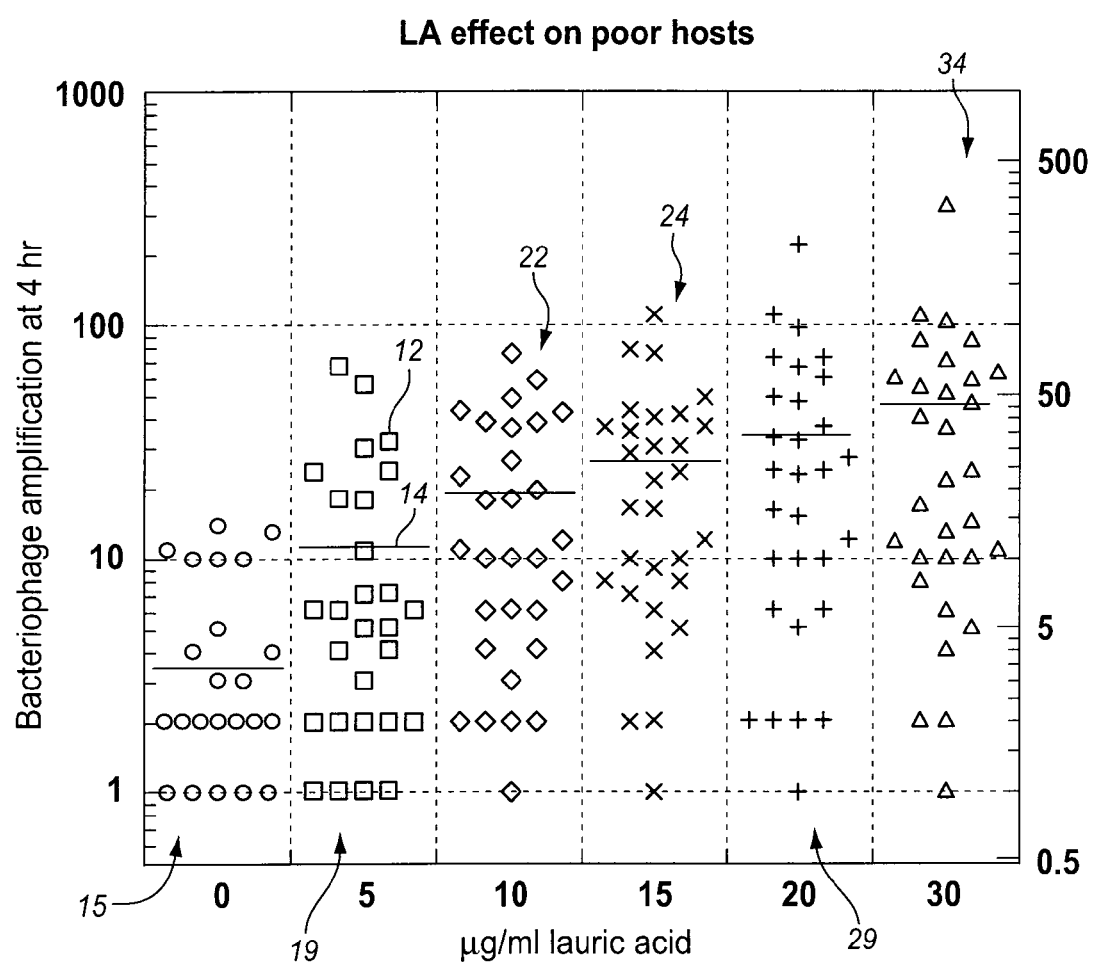
FIG. 1 is a graph indicating the addition of lauric acid improves amplification on poor or restrictive *S. aureus* hosts.

The invention relates to the use of bacteriophage to detect microorganisms. Bacteriophage are viruses that have evolved in nature to use bacteria as a means of replicating themselves. A phage does this by attaching itself to a bacterium and injecting its DNA (or RNA) into that bacterium and inducing it to replicate the phage hundreds or even thousands of times. This is referred to as phage amplification. As summarized in the Background of the Invention above, there is much literature based on the idea that phage amplification can potentially provide a marker indicative of the bacterium that can be detected more easily and more rapidly than the bacterium itself. A fundamental principle that allows particular bacteria to be detected via bacteriophage amplification followed by an assay of a bacteriophage marker is that a particular bacteriophage will infect only a particular bacterium. That is, the bacteriophage is specific to the bacteria. Thus, if a particular bacteriophage that is specific to particular bacteria is introduced into a sample, and later the bacteriophage has been found to have multiplied, the bacteria to which the bacteriophage is specific must have been present in the sample. In this way, the prior art teaches that bacteriophage amplification can be used to identify specific bacteria present in a sample. However, bacteriophage that are 100% specific to a single bacteria species that it is desired to detect are not present in nature. Further, bacteriophage found in nature also are not 100% sensitive to the bacteria that it is desired to detect. Because the bacteriophage found in nature are imperfect as to these desired qualities, a commercially viable bacteria detection process has been much more difficult to arrive at than was at first hoped. This application discloses systems and processes that enhance bacteriophage amplification and bacteriophage sensitivity and, thus, lead for the first time to the possibility of a commercially viable process. As summarized above, the invention provides substances and processes that enhance bacteriophage amplification without reducing specificity or sensitivity. In fact, as will be shown below, the substances and processes of the invention not only enhance amplification but increase sensitivity.

In this disclosure, the terms "bacteriophage" and "phage" include bacteriophage, phage, mycobacteriophage (such as for TB and paraTB), mycophage (such as for fungi), mycoplasma phage or mycoplasmal phage, and any other term that refers to a virus that can invade living bacteria, fungi, mycoplasmas, protozoa, yeasts, and other microscopic living organisms and uses them to replicate itself. Here, "microscopic" means that the largest dimension is one millimeter or less.

In this disclosure, a bacteriophage marker is any biological or organic element that can be associated with the presence of a bacteriophage. Without limitation, this may be the bacteriophage itself, a lipid incorporated into the phage structure, a protein associated with the bacteriophage, RNA or DNA associated with the bacteriophage, or any portion of any of the foregoing. In this disclosure, a bacterial marker is any biological or organic element that is released when a bacterium is lysed by a bacteriophage, including cell wall components, bacterial nucleic acids, proteins, enzymes, small molecules, or any portion of the foregoing.

Figure 2:
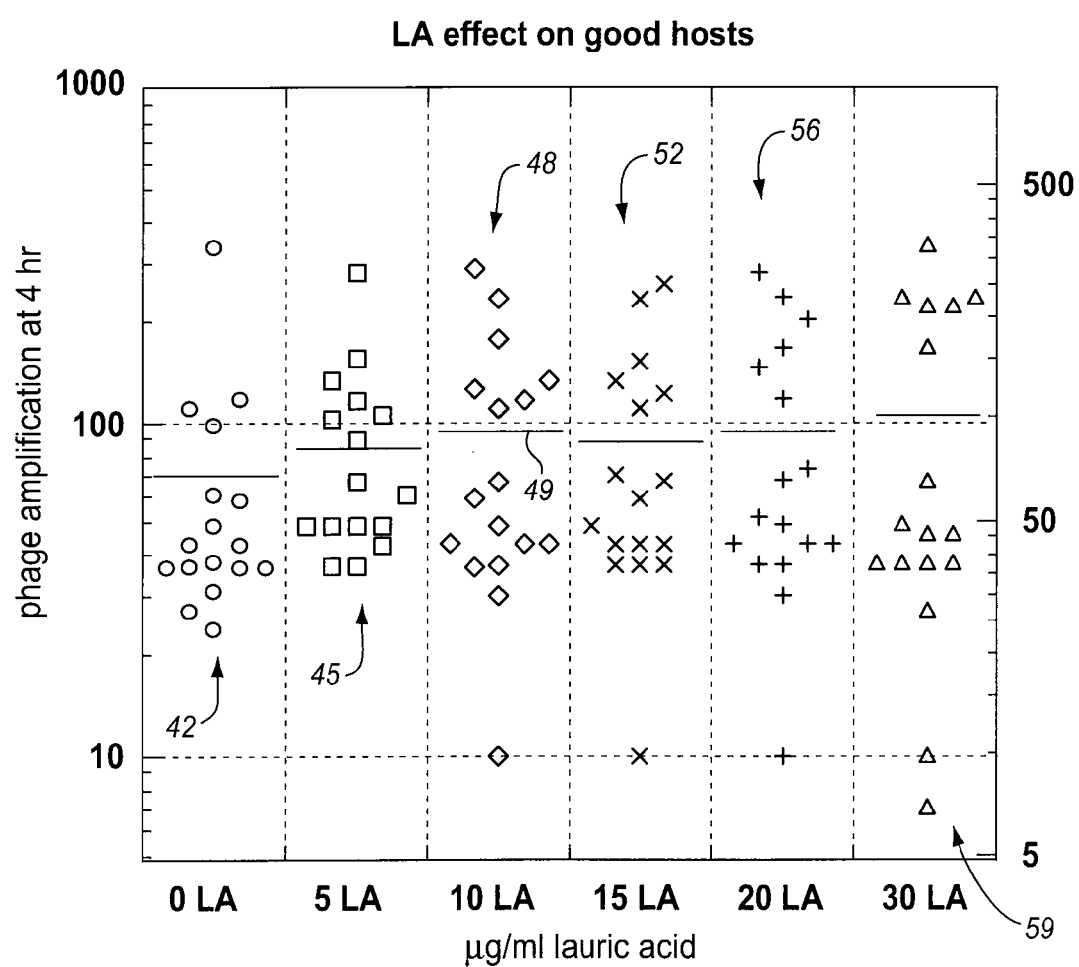
FIG. 2 is a graph indicating lauric acid increases bacteriophage amplification on permissive *S. aureus* hosts.

In FIGS. 1 and 2, each symbol, such as 12, represents an independent clinical isolate of *S. aureus*, Clinical isolates of *S. aureus* were grown in BacTec Aerobic F/10 broth charged with 20% blood at 35° to a density of approximately $10^8$ cfu/ml. An aliquot of these cultures was then diluted 1:250 into a test mixture of Tryptic Soy Broth containing bacteriophage strains MP112 and MP115, each at $10^7$ pfu/ml, and varying concentrations of lauric acid. The cultures were grown for four hours at 35°, then diluted and plated on bacterial lawns using the top agar method. After overnight incubation, pfu/ml for each culture was calculated from the plates and divided by input pfu/ml to obtain the value for amplification plotted in FIG. 1. The results for these isolates with no lauric acid are shown at 15; the results for a concentration of 5 μg/ml of lauric acid are shown at 19; the results for a concentration of 10 μg/ml of lauric acid are shown at 22; the results for a concentration of 15 μg/ml of lauric acid are shown at 26; the results for a concentration of 20 μg/ml of lauric acid are shown at 29; and the results for a concentration of 30 μg/ml of lauric acid are shown at 34. Within these concentrations, the average level of amplification increases from three-fold with no lauric acid to 45-fold at 30 μg/ml lauric acid. The average level of amplification is shown by the solid line, such as 14, in each of the columns.

The set of isolates used in FIG. 1 is known from previous experiments to be resistant to bacteriophage infection or to amplify bacteriophage poorly after infection. The 28 strains in this study were chosen from a collection of 202 clinical isolates as the poorest hosts for bacteriophage amplification. Given that these strains represent ~14% of the collection, it is plausible that most or all are TSS-positive; and lauric acid enhances phage amplification through suppression of TSS gene expression. However, we find that lauric acid, and by extension other fatty acids, generally promotes bacteriophage amplification in nearly all hosts tested. This novel result indicates that TSS suppression is not sufficient to explain the effect of fatty acids on bacteriophage amplification.

The effect of lauric acid on good bacteriophage hosts is shown in FIG. 2. The results for these isolates with no lauric acid are shown at 42; the results for a concentration of 5 μg/ml of lauric acid are shown at 45; the results for a concentration of 10 μg/ml of lauric acid are shown at 48; the results for a concentration of 15 μg/ml of lauric acid are shown at 52; the results for a concentration of 20 μg/ml of lauric acid are shown at 56; and the results for a concentration of 30 μg/ml of lauric acid are shown at 59. The average amplification in this group increases from 69-fold to over 100-fold with the addition of lauric acid. The average level of amplification is shown by the solid line, such as 49, in each of the columns. To date, more than 80% of *S. aureus* strains tested show stimulation of bacteriophage amplification in response to lauric acid.

Figure 3:
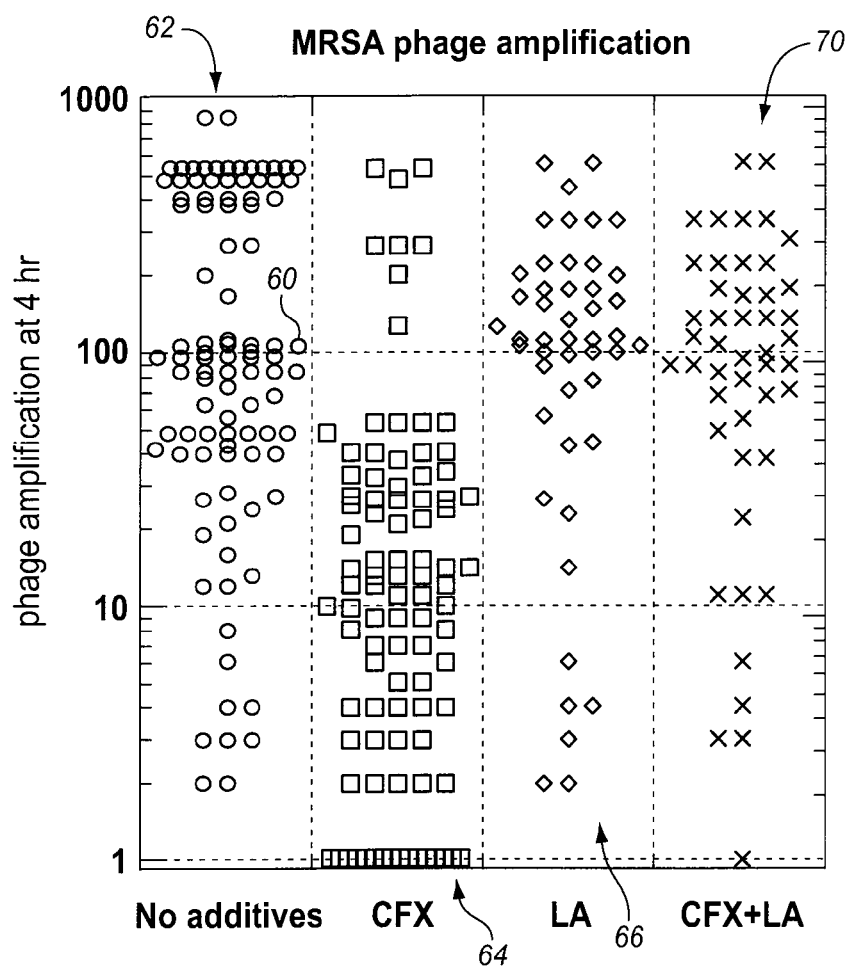
FIG. 3 is a graph indicating lauric acid relieves suppression of phage amplification by cefoxitin in MRSA strains.

Lauric acid, other fatty acids, and their derivatives ameliorate the effects of β-lactam antibiotics on phage amplification in methicillin-resistant *S. aureus* (MRSA) hosts, as shown in FIG. 3. This property enhances the performance and utility of bacteriophage-based tests in detecting, classifying, and distinguishing MRSA from methicillin-susceptible *S. aureus* (MSSA). In FIG. 3, each symbol represents a clinical MRSA (methicillin-resistant *S. aureus*) isolate able to grow in the presence of β-lactam antibiotics such as cefoxitin. The first column 62 (circles) indicates amplification by MRSA strains with no cefoxitin and no lauric acid. The second column 64 (squares) indicates amplification with added cefoxitin. Note the suppression of phage amplification. The third column 66 (diamonds) indicates amplification with added lauric acid. The fourth column 70 (x's) indicate amplification with added lauric acid and cefoxitin. This shows that lauric acid relieves suppression of phage amplification by cefoxitin in MRSA strains.

Other fatty acid compounds that positively stimulate bacteriophage amplification include saturated fatty acids: caproic acid, caprylic acid, capric acid, and myristic acid; conjugated fatty acids: glycerol monolaurate; and unsaturated fatty acids: oleic acid and linoleic acid. For the purposes of this invention, the term "fatty acid" shall refer to all such compounds and related compounds.

Figure 4:
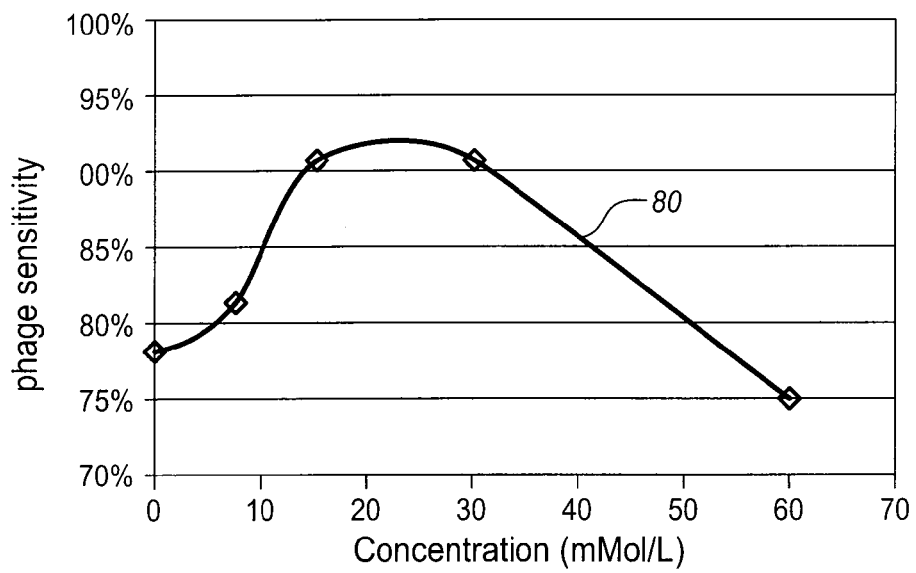
FIG. 4 is a graph showing bacteriophage sensitivity in percent versus concentration of sodium pyruvate in mmol/L.
Figure 5:
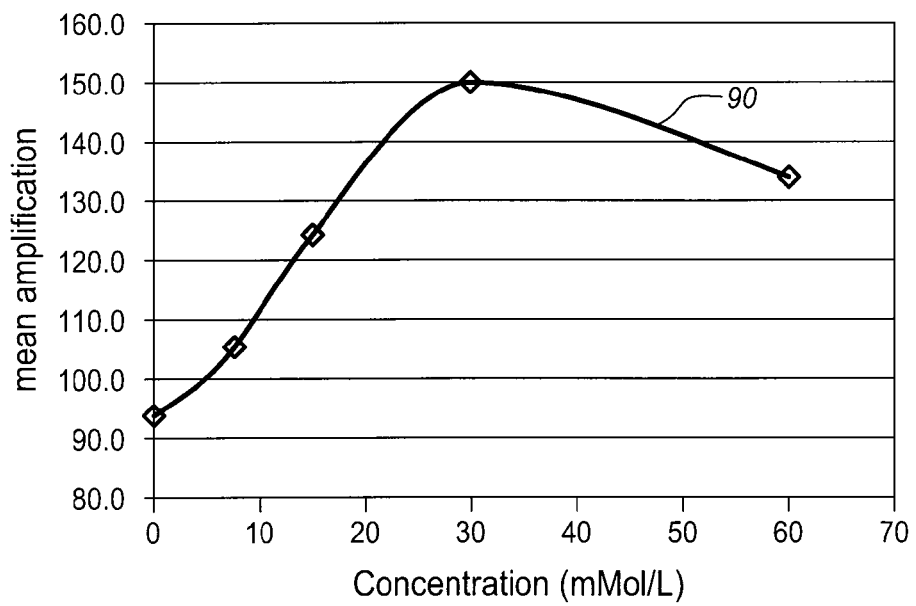
FIG. 5 is a graph showing bacteriophage mean amplification versus concentration of sodium pyruvate in mmol/L.

Pyruvic acid is a metabolic compound linking aerobic and anaerobic metabolism to carbohydrate, fatty acid, and amino acid synthesis. As bacteriophage amplification imposes substantial metabolic demands on the host, after discovery of the results shown in FIGS. 1-3, we reasoned that supplementing the bacteriophage host growth medium with this compound might stimulate bacteriophage amplification, leading to better assay performance. FIGS. 4 and 5 show the effect of medium supplementation by sodium pyruvate. FIG. 4 is a graph showing a curve 80 of measured bacteriophage sensitivity in percent versus concentration of sodium pyruvate in mmol/L. A panel of 32 *S. aureus* strains was grown in charged BacTec SA blood culture medium to mid-log phase, and then diluted into growth medium containing bacteriophage and the indicated concentrations of sodium pyruvate in mmol/L. After 4 hours of incubation at 35°, the cultures were tested for bacteriophage amplification by standard microbiological methods. Strains showing significant amplification, defined as >8-fold over input bacteriophage, were scored as positive. Sensitivity is defined as the number of positive strains as a percentage of all strains tested. As can be seen from the graph, the addition of from 12 mmol/L to 37 mmol/L of sodium pyruvate was found to increase phage sensitivity in these strains from about 78% to between 87% and 92%. The range of concentrations of from 15 mmol/L to 31 mmol/L resulted in sensitivity above 90%. At 27 mmol/L concentration, the sensitivity was increased about 15% over sensitivities without sodium pyruvate. The data indicate that supplementation of growth media with sodium pyruvate can significantly enhance the fraction of strains able to amplify bacteriophage.

FIG. 5 is a graph showing a curve 90 of measured bacteriophage mean amplification versus concentration of sodium pyruvate in mmol/L. The difference in amplification between 0 mM (millimoles) pyruvate and 15 or 30 mM is significant when tested by the Student's paired t-test (p=0.002, 0.005, respectively). The mean amplification of the bacteriophage was increased significantly in a range of from about 10 mmol/L to 60 mmol/L. For example, the mean amplification increased from about 92 without sodium pyruvate to 150 at about 30 mmol/L of sodium pyruvate. These data show that addition of sodium pyruvate to growth medium leads to improved amplification of bacteriophage and thereby to improved performance of tests and assays based on bacteriophage amplification.

The methods and substances that enhance bacteriophage amplification are preferably used in combination with substances and methods that inhibit replication in potentially cross-reactive, non-target bacteria, and use this inhibition to increase the selectivity of the phage-based diagnostic process. We shall describe three embodiments of the inhibition process herein: 1) inhibiting the growth of potentially cross-reactive bacteria while allowing growth of the target bacteria, 2) selectively removing potential cross-reactive bacteria from a sample using selective binding agents attached to some support (i.e., microparticles), and 3) selectively destroying potentially cross-reactive bacteria. These embodiments are intended to be illustrative, though the invention is not limited to these embodiments. Other methods with the same results can be contemplated by those skilled in the arts.

Inhibition of potentially cross-reactive bacteria can be accomplished using methods common to microbiological detection. For example, substances such as sodium chloride (in high concentration), Polymyxin B, Polymyxin E, other Polymyxins, and metal compounds, such as potassium tellurite, inhibit the growth of some coagulase negative Staphylococcus (CNS) while allowing the growth of S. aureus, These compounds can also significantly inhibit or retard replication of bacteriophage in CNS while minimally affecting replication in S. aureus, The usage of selective media to differentially affect the efficiency and timing of phage replication is a novel method for improving the specificity of bacteriophage-based bacterial diagnostic methods.

Removal of non-target bacteria may be accomplished using antibodies, bacteriophage selective for the non-target bacteria, or other compounds that selectively bind to non-target bacteria. For an S. aureus test, removal of CNS species can be beneficial. Binding of these compounds to non-target bacteria may be sufficient to block the binding of bacteriophage to those bacteria, preventing successful infection and replication. Alternatively, these compounds may be attached to other substrate such as micro-particles, magnetic beads, or solid substrates. When incubated with a sample, potential non-target bacteria will selectively bind to the substrate. The substrate then can be physically removed from the sample. Separation methods include centrifugation for micro-particles or by the application of a magnetic field for magnetic beads.

Selective destruction of non-target bacteria can be accomplished using antibacterial compounds that selectively destroy non-target bacteria such that they are not susceptible to phage infection while leaving target bacteria largely unharmed and susceptible to phage infection. Such compounds include: a) selective antibiotics, and b) bacteriophage that selectively bind to and/or infect potentially cross-reactive, non-target bacteria. The latter are complementary bacteriophage to the primary bacteriophage used to selectively infect the target bacteria in the sample. Complementary bacteriophage can destroy non-target bacteria by successfully infecting and lysing those non-target bacteria such that phage infection by the primary bacteriophage is eliminated or significantly reduced. Complementary bacteriophage can also be used to destroy non-target bacteria by a process known as lysis from without. Lysis from without refers to the destruction of a bacterium when hundreds or thousands of phage particles bind to its cell wall. This process can be utilized in this invention by adding a high concentration of complementary phage to the sample such that large numbers of complementary phage quickly and selectively bind to potentially cross-reactive bacteria. Under pressure of multiple phage binding, the cross-reactive bacteria can be made to burst, eliminating them as a locus for phage infection by the prime bacteriophage.

As described in International Patent Application No. PCT/US07/085268 filed Nov. 20, 2007, which is incorporated herein by reference, bacteriophage can be used to detect bacteria simply using the property that phage attach to the bacteria, that is, without the amplification step. This application also discloses how bacteriophage can be used to determine the antibiotic susceptibility or antibiotic resistance of a microorganism. It is contemplated by the invention that the materials and processes described herein can also be used to advantage in any of the foregoing processes and systems. Many other phage-based methods and apparatus used to identify the microorganism and/or to determine the antibiotic resistance test or antibiotic susceptibility can be enhanced by the method and apparatus of the invention.

It should be understood that the particular embodiments shown in the drawings and described within this specification are for purposes of example and should not be construed to limit the invention which will be described in the claims below. For example, now that it has been found that lauric acid enhances bacteriophage amplification, it is evident that other, related substances may also enhance bacteriophage amplification. As another example, since the reasoning with respect to pyruvate has been shown to be correct, those skilled in the art will be able to follow such reasoning to other substances that will enhance bacteriophage amplification and/or phage sensitivity. Further, it is evident that those skilled in the art may now make numerous uses and modifications of the specific embodiment described without departing from the inventive concepts. Several examples are described herein. Equivalent structures and processes may be substituted for the various structures and processes described; the subprocesses of the inventive method may, in some instances, be performed in a different order; or a variety of different materials and elements may be used. Consequently, the invention is to be construed as embracing each and every novel feature and novel combination of features present in and/or possessed by the microorganism detection apparatus and methods described.

What is claimed as new and desired to be protected by Letters Patent of the United States is:

1. A method of determining the presence or absence of a target microorganism in a sample to be tested, said method comprising:
   combining with said sample a growth medium and an amount of bacteriophage capable of attaching to said target microorganism to create a bacteriophage exposed sample;
   providing conditions to said bacteriophage-exposed sample sufficient to allow said bacteriophage to infect said microorganism; and
   assaying said bacteriophage-exposed sample to detect the presence or absence of a bacteriophage marker to determine the presence or absence of said target microorganism;

wherein said combining comprises combining with said bacteriophage and said target microorganism a substance which enhances bacteriophage amplification in said target organism while increasing bacteriophage sensitivity to said target microorganism, said substance being different than said growth medium, said substance being lauric acid.

2. A method as in claim 1 wherein said microorganism is a bacterium, and said assaying comprises detecting said bacteriophage marker as an indication of the presence of said target bacterium in said sample.

\* \* \* \* \*